United States Patent [19]

Riederer et al.

[11] Patent Number: 4,694,252

[45] Date of Patent: Sep. 15, 1987

[54] AUTOMATED ESTIMATION OF T1 AND T2 RELAXATION TIMES

[75] Inventors: Stephen J. Riederer; Ronald C. Wright; James N. Lee, all of Durham, N.C.

[73] Assignee: Duke University, Durham, N.C.

[21] Appl. No.: 824,784

[22] Filed: Jan. 31, 1986

Related U.S. Application Data

[63] Continuation-in-part of Ser. No. 734,101, May 15, 1985, Pat. No. 4,641,095.

[51] Int. Cl.$^4$ ............................................. G01R 33/20
[52] U.S. Cl. .................................... 324/309; 324/312; 324/307
[58] Field of Search ............... 324/300, 308, 307, 309, 324/312, 313; 364/414

[56] References Cited

U.S. PATENT DOCUMENTS

| | | | |
|---|---|---|---|
| 4,284,948 | 8/1981 | Young | 324/309 |
| 4,634,979 | 1/1987 | Riederer | 324/307 |
| 4,641,096 | 2/1987 | Kamo et al. | 324/307 |

Primary Examiner—Michael J. Tokar
Attorney, Agent, or Firm—Oblon, Fisher, Spivak, McClelland, & Maier

[57] ABSTRACT

A method of calculating the intrinsic parameters including the spin-lattice relaxation time T1 and the spin-spin relaxation time T2 for Nuclear Magnetic Resonance (NMR) technique which utilizes calculations of derived algorithms by a series of passthroughs of a digital video processor. The use of a digital video processor to accomplish the algorithm construction provides a significant increase in the speed with which the intrinsic parameters can be calculated.

9 Claims, 13 Drawing Figures

FIG. 8

AUTOMATED ESTIMATION OF T1 AND T2 RELAXATION TIMES

The U.S. Government has a paid-up license in this invention and the right in limited circumstances to require the patent owner to license others on reasonable terms as provided for by the terms of Grant No. R01CA37993 awarded by National Institutes of Health.

This application is a continuation-in-part of the copending Application Ser. No. 734,101 filed May 15, 1985, now U.S. Pat. No. 4,641,095.

BACKGROUND OF THE INVENTION

1. Field of the Invention

This invention relates to a method for providing automated estimation of the intrinsic properties of materials subjected to Nuclear Magnetic Resonance spectroscopy and imaging. In particular, the invention concerns an improved system for rapidly determining the spin lattice relaxation time T1 and the spin-spin relaxation time T2, each of which are directly related to the specific properties of a tissue which is being studied.

2. Discussion of the Background

Nuclear magnetic resonance (NMR) has recently become extremely popular for the reproduction of images of the interior portions of the human body for diagnostic purposes. Although the examination of the interior body or a body portion having a variety of relatively soft tissues is the primary use for NMR techniques, they can also be utilized for circumstances whereby characteristics of tissues under inspection can be portrayed which are ordinarly not readily obtained using a radiography or other imaging techniques.

The fundamental description of basic NMR physics and imaging techiques is found in Kaufmann et al., Nuclear Magnetic Resonance Imaging in Medicine, IGAKU-SHOIN Medical Publishers, Inc., New York and Tokyo (1981). The important features of the NMR technique which are commonly used in previous methods will now be elaborated upon.

The body under examination is subjected to one magnetic field which is usually constant in magnitude and another field which lies along at least one different vector from the first magnetic field. The second magnetic field is usually time-varying with the exact characteristic of each of these fields being a function of choice between any one of several available imaging techniques. During NMR examinations, the characteristics of the field energy must be preselected. selected. As an example, one of the techniques called spin-echo imaging, utilizes a pre-selected repetition time $T_R$, which is defined as the time between successive application of the same pulse sequence. Also pre-selected is the sampling delay time t (TAU) which is often set equal to TE/2 where TE is the time at which a spin-echo is measured. The first and second fields are applied to the tissue being examined in accordance with selected times and the results are detected and stored with the levels of the storage signals being correlated with their physical positions and with these levels being represented by a matrix of numbers. The numbers of the matrix are then displayed as a matrix of points of pixels which have different light or dark levels and the composite of these pixels forms an image having various contrasting areas.

A physician utilizes the results of these contrasting areas within the image to observe and analyze a "slice" of the body of which the image was made from and, in a medical context, to thereby form a diagnosis. The degree of contrast between the various areas is a function of $T_R$ and t values which are selected before the measurement is made. The degree of contrast is also a function of the intrinsic properties of the materials including the net magnetization $M_O$ (which is proportional to Proton density), and the relaxation times T1 and T2. While one particular set of values for $T_R$ and t will produce an image with excellent contrast between certain sets of materials, it must be noted that this contrast will probably be insufficient between other types of materials being used. As a result of this varying contrast which depends upon the materials being used, it is necessary to make numerous sets of measurements with various values for $T_R$ and t . The images which result from these measurements use these different values of $T_R$ and t in order to adequately examine various tissues involved.

This time consuming process in which the patient is often subjected to discomfort and sometimes repeatedly subjected to the effects of strong directional magnetic fields has been alleviated in accordance with the method and apparatus disclosed in copending Application Ser. No. 727,674 filed Apr. 26, 1985, of which the present inventor is a coinventor. Utilizing the method and the apparatus of the copending application an apparatus is disclosed which is capable of obtaining intrinsic parameters of the body materials under examination and forming synthetic images based on those intrinsic parameters in order to permit the synthesis of images formed on the basis of other selectable parameters. The technique of the copending application provides a method in which a minimal number of measurements can be made and in which the data derived from these measurements is used to form synthetic images which include tissue contrast of a type which would have been produced by measurements made with selected parameters such as $T_R$ and t values other than those which are actually used for the measurements.

Even with respect to the improved overall apparatus and method for obtaining intrinsic parameters of the above identified copending application, there still exists a problem with respect to the actual determination of the intrinsic parameters from physically measured values. These intrinsic parameters, and more specifically the relaxation time T1, are generally found by acquiring NMR signals for several different repetition times $T_R$ and plotting them as a function of time. The value of the spin lattice relaxation time T1 is substantially a measure of the curvature of the smooth curve which most closely matches the measured signals. Because of the statistical uncertainty in the measured signals, there is uncertainty in the computed value of T1. Generally, this can only be compensated for by taking measurements several times at the repetition times initially used or by taking measurements at additional repetition times. In both cases the total scanning time can be increased.

Additional background information and disclosure of devices and techniques in the field to which this invention relates can be found in the following articles and U.S. patents.

F. W. Wehrli, J. R. McFall, and G. H. Glover. The dependence of nuclear magnetic resonance (NMR) image contrast on intrinsic and operator-selectable parameters presented at the meeting of the SPIE, Medicine XII, volume 419, April 1983.

I. R. Young, et al. Contrast in NMR Imaging. Presented at the Society of Magnetic Resonance in Medicine, August 1983.

D. Ortendahi, et al. Calculated NMR images. Presented at the Society of Magnetic Resonance in Medicine, August 1983.

P. L. Davis, et al. Optimal spin-echo images for liver lesions by retrospective calculations. Presented at the Society of Magnetic Residence in Medicine, August 1983.

| U.S. Pat. No. | Inventor |
|---|---|
| 3,789,832 | Damadian |
| 4,045,723 | Ernst |
| 4,284,948 | Young |
| 4,292,977 | Krause et al |
| 4,297,637 | Crookes et al |
| 4,307,343 | Likes |
| 4,318,043 | Crookes et al |
| 4,354,499 | Damadian |
| 4,355,282 | Young et al |
| 4,390,840 | Ganssen et al |

SUMMARY OF THE INVENTION

Accordingly, one object of the present invention is to provide a method and an apparatus for generating images of the spin-lattice relaxation time T1 and the spin-spin relaxation time at high speed through the use of algorithms which are implemented on a real time digital video processor which has several digital frame memories used for storing original images, intermediate results and the final T1 or T2 image.

It is another object of the present invention to utilize a method and apparatus whereby a digital video processor utilizes a particular algorithm for calculating T1 from two measurements.

It is another object of the present invention to provide a method and apparatus whereby the high speed circuitry of the digital video processor provides for a calculation of the spin-spin relaxation T2 from two measurements using a second algorithm.

It is a further object of the present invention to utilize a third algorithm for calculating the spin-spin relaxation time from an arbitrary number of measurements through the use of the digital video processor (DVP).

It is a another object of the present invention to provide for the solution to algorithms for the spin-lattice relaxation time T1 and the spin-spin relaxation time T2 which are implemented as a sequence of passes through a digital video processor (DVP) with each pass requiring 1/30 sec. and wherein between each pass, the DVP is reconfigured to perform the next desired mathematical step of the algorithm.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
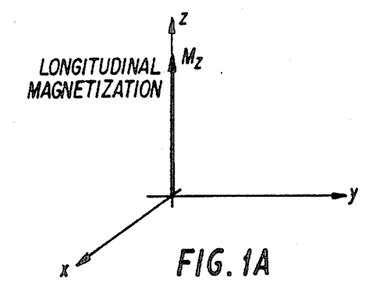
FIGS. 1A and 1B are graphical representation of the longitudinal and transverse magnetization, respectively.
Figure 1B:
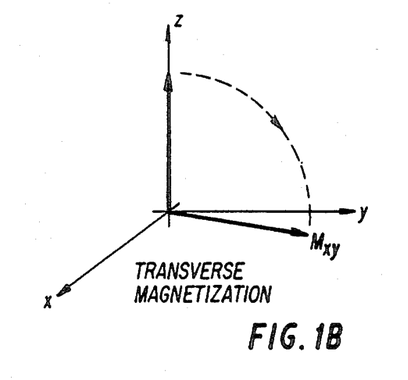

Referring now to the drawings, wherein like reference numerals designate identical or corresponding parts throughout the several views, and more particularly to FIG. 1A thereof, there is illustrated a graphical representation of the longitudinal magnetization parameter ($M_z$) which is aligned in the z axis of the xyz coordinate system. Because the quantity which is to be measured is the spin lattice relaxation time T1, which is defined as the recovery time of the longitudinal magnetization $M_z$ after it has been altered away from its equilibrium position $M_O$, this concept with respect to the longitudinal magnetization is a first step in developing a determination of T1. The FIG. 1B illustrates the "flipping" of the magnetization into a transverse plane (x-y). $M_z$, illustrated in FIG. 1, is never measured directly but is subjected to the flipping shown in FIG. 1B. The length of the "flipped" magnetization $M_{xy}$, immediately after the flip, equals that of $M_z$ prior to the flip. Because the measurement of T1 is actually the recovery time of the longitudinal magnetization after it has been altered away from an equilibrium position $M_O$, the process naturally involves the initial setting of the $M_z$ at a known quantity such as O or $-M_O$.

Figure 2A:
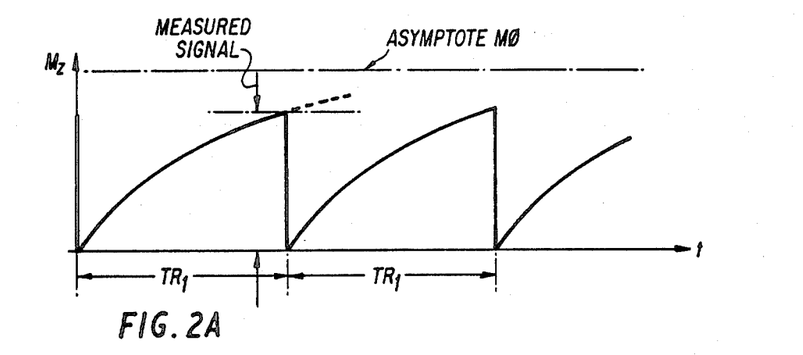
FIG. 2A and 2B are a graphical representation of the behavior of the length of the longitudinal magnetization as a function of time at different repetition times $T_R$.
Figure 2B:
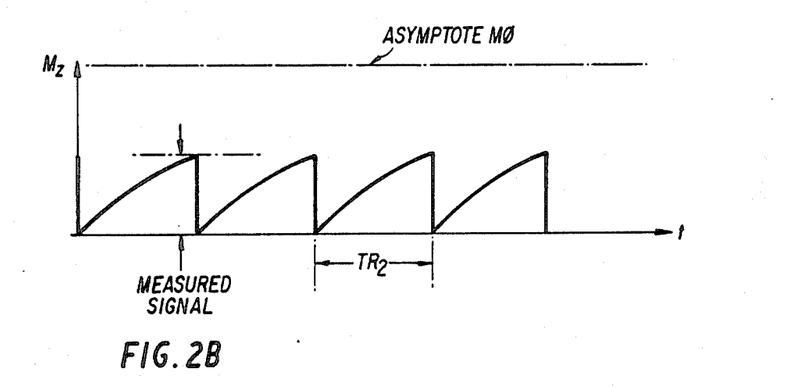

The FIG. 2A illustrates that the magnetization $M_z$ is initially set at a 0 value and then begins to change as a function of time toward asymptote $M_O$. After some selected repetition time TR2 the signal is measured and the magnetization is returned to the starting initial value or 0 in the instance of FIG. 2A. The FIG. 2B illustrates a value of $TR_1$ which is less than $TR_2$ for purposes of providing a measured signal. It can be seen that the time period $TR_1$ is less than $TR_2$ so that the measured signal is less for a shorter time period or in other words the magnetization has not had as much opportunity to approach the asymptotic value as in the instance of FIG. 2A which has a longer value for TR.

Figure 3:
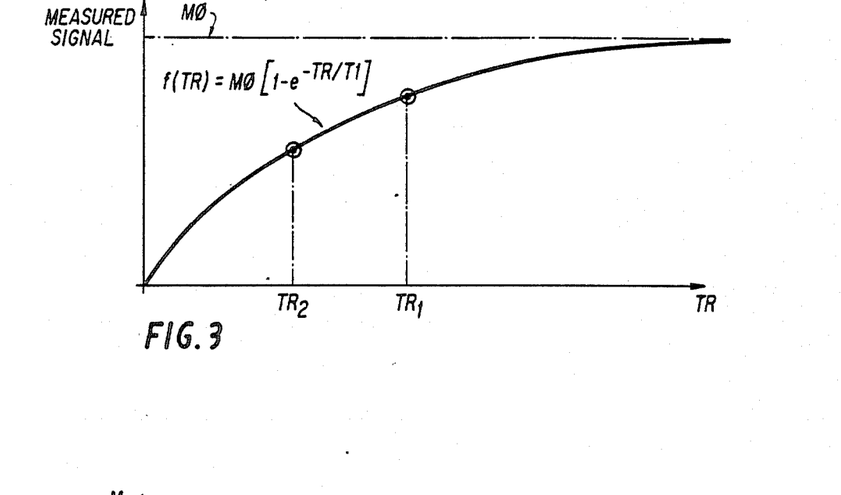
FIG. 3 illustrates a plotting of the measurements made from FIGS. 2A and 2B with respect to estimating T1 utilizing a characteristic equation.
Figure 7:
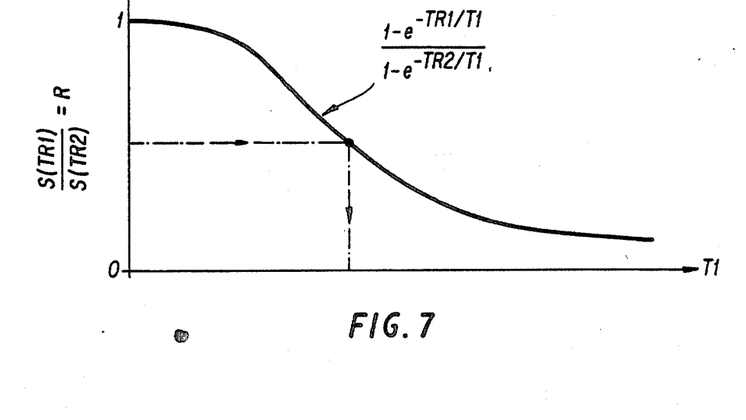
FIG. 7 is a graphical representation of the actual determination of T1 for measurements at two TR times.

The FIG. 3 illustrates how the measurements made from FIGS. 2A and 2B are plotted and that these values fit along a curve defined by the equation such that the measured signal is a function of the asymptote and TR as well as T1. More specifically, $S(TR) = M_O[1 - \exp(-TR/T1)]$ from the measured signals as reflected by FIG. 3 and the known values which are utilized for TR1 and TR2 a first estimate can be made with respect to T1. The actual determination from the measurements of two different TR times is shown in FIG. 7 wherein the equation S(TR) for each of two different values TR1 and TR2 are divided in order to form a ratio R wherein $R = S(TR1)/S(TR2) = M_O[1-\exp(-TR1/T1)]M_O(1-\exp(-TR2/T1)$ wherein R is the ratio of the two measurements for TR1 and TR2. The ratio of the expressions on the right side of the equation are a function of TR1 and TR2 (known quantities) and T1 (the desired unknown). FIG. 7 shows a plot of this ratio and from the knowledge of the value of R, i.e., from a knowledge of the values of the measured signals, the FIG. 7 yields a value for T1, as shown.

Figure 4A:
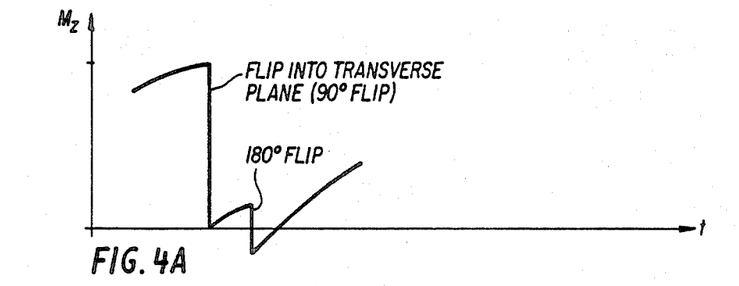
FIGS. 4A and 4B detail the measurement process for a conventional single spin-echo.
Figure 4B:
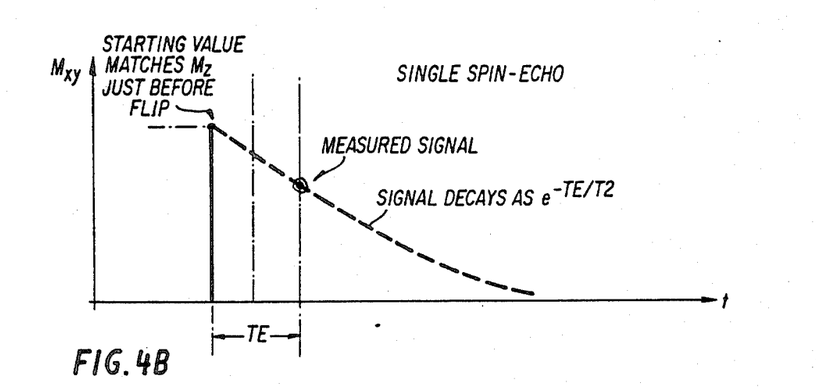

A single spin-echo treatment is shown in FIG. 4A which involves a flipping of the longitudinal magnetization into the transverse plane in a manner similar to the showings of FIGS. 1A and 1B. This is a 90° flip and the starting value, as shown in FIG. 4B, in the x-y plane for the magnetization $M_{xy}$ is equal to the longitudinal magnetization $M_z$ just prior to the flip. At a time period TE/2 a 180° flip occurs which basically involves going from a plus value to an equivalent negative value, ergo 180°. When the signal after the 180° flip recovers to the zero point or in other words after a value of TE from the initial 90° flip, a measured signal is obtained as shown in FIG. 4B. The decay of the signal value from the starting value through the measured value at time TE is controlled by the exponential function EXP $(-TE/T2)$.

Figure 5A:
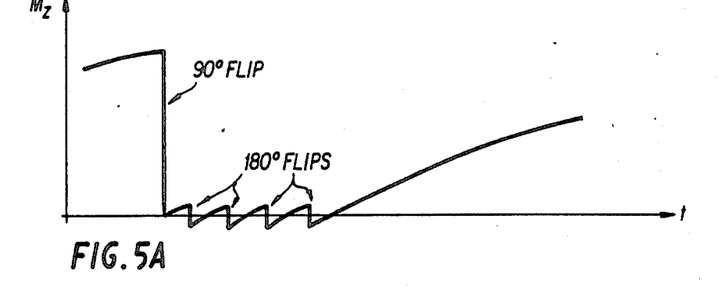
FIGS. 5A and 5B show the instance of a multiple spin-echo analogous to the FIG. 4 measurement.
Figure 5B:
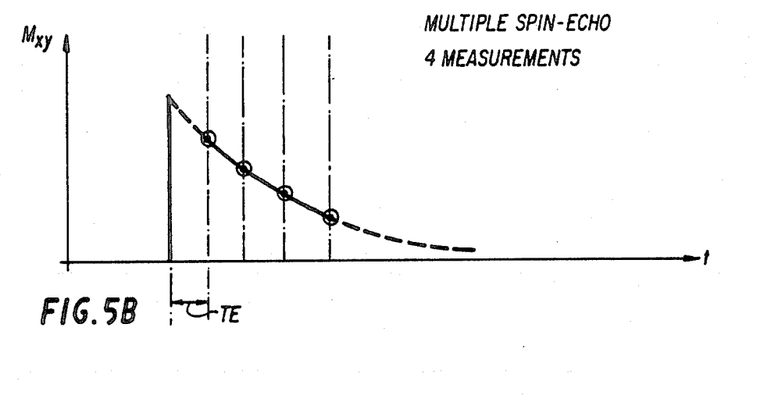

In FIGS. 5A and 5B, there is shown a graphic illustration of the application of the multiple spinecho technique. This provides for an increased number of measurements without an increased number of scans.

Figure 6:
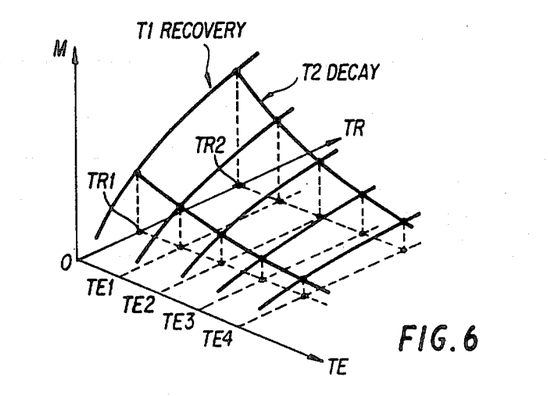
FIG. 6 is a three-dimensional plot of the magnetization of an arbitrary material which is measured in a spin-echo treatment as a function of the repetition time $T_R$ and the echo times TE.

The FIG. 6 illustrates a three-dimensional graph which shows the relationship between the longitudinal magnetization M, the repetition times TR and the spin-echo times TE. Essentially, FIG. 6 can be seen as an imposition of FIG. 3 onto FIG. 5B. It is important to note that T2 is not essential with respect to the calculation of T1 because as seen from FIG. 7, for a single estimate of T1, the T2 is not a necessary function and is not a required quantity for the determination of T1.

Figure 8:
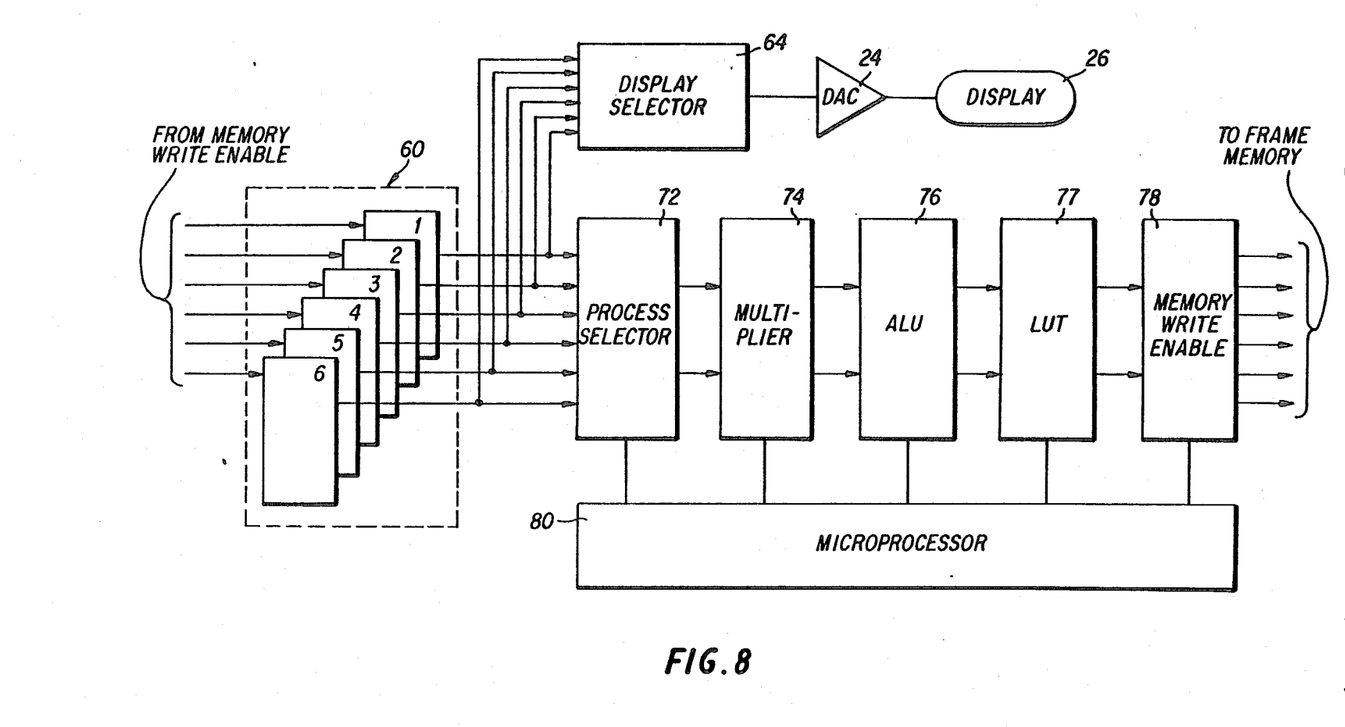
FIG. 8 is a block diagram of a digital video processor apparatus utilized to effect the method of the invention.

The aforementioned method for determination of T1 can be accomplished by the apparatus shown in FIG. 8, although those skilled in the art would recognize that other image synthesis apparatus configurations would be capable of carrying out the aforementioned method.

The microprocessor controller 80 provides the overall control of the digital video processor units 72, 74, 76, 77, 78 and 64.

During a first time period the signals measured for every pixel for each of the two TR (repetition times) is stored in the individual frame memories 1 and 2 as the function S(TR1) and S(TR2), respectively. The reciprocal of S(TR2) is obtained by passing the value of frame memory 2 through the high speed look up table 77 and during the same frame interval the reciprocal image obtained in look up table 77 is stored back into frame memory 2.

In the next step the product of frame memories 1 and 2 i.e., $S(TR1) \times 1/S(TR2)$, is utilized to obtain the "ratio" image $R = S(TR1)/S(TR2)$. This is accomplished through the use of the high speed multiplier 74 and the result of this multiplication is sent back to frame 2.

In the final step the ratio image R is read out from the frame 2 and passed through the LUT 77 which is now loaded with the transfer function previously discussed and shown in FIG. 7. More specifically the transfer function which is loaded into the look up table 40 is given by the equation $[1-\exp(-TR1/T1)]/[1-\exp(-TR2/T1)]$. Thus for a value of R stored in the frame memory 2, the look up table 77, programmed with the above algorithm by the microprocessor 80 provides an output T1 which is fed back and stored in the frame memory 2.

Because the value of T1 is not available by analytical methods from the equation $R = [1-\exp(-TR1/T1)]/1-\exp(-TR2/T1)]$ the microprocessor forms a table of values for each of a known set of TR1 and TR2 by for example setting T1 equal to one and solving for R and then setting T1 equal to two solving for $R_2$ etc., with the values of R commonly decreasing from 1.00 to approximately 0.4. This sets up a table of values for T1 which is a consecutive integer table whereas the values for R do not maintain a constant difference between two consecutive values. At this point the values of R are set as for example 1.000, 0.999, 0.998, etc., down to 0.400 with corresponding values for T1 being determined by interpolation. Thus when a particular R value is retained in the memory frame 2, the the look up table 77 goes to the value for R and takes the corresponding value from the table for the value of T1. The advantage of using the digital video processor is that because $TR_1$ and $TR_2$ are known combinations or they are a variety of known combinations, each of the calculations of the equation can be determined and stored beforehand for various values of TR1 and TR2 which are typically used in NMR techniques. Thus the only thing left for the look up table 77 to accomplish given a value of R is to go to the appropriate stored value for T1 according to whichever values of TR2 and TR1 are used.

Thus, the invention which has been described provides for an improved method of determining the T1 relaxation time which can be accomplished with a significantly reduced calculation time in the order of 1–2 seconds because each pass through of the digital video procesor requires but 1/30 seconds when contrasted with the 30 seconds of the prior art methods utilizing a programmable computer.

Figure 9:
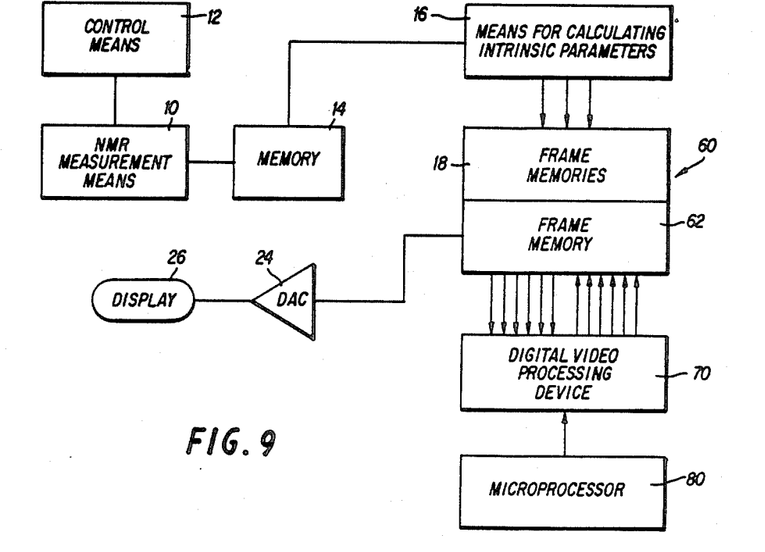
FIG. 9 is a block diagram of the measurement system of NMR techniques as constructed with a means for calculating instrinsic parameters corresponding to the digital video processor of FIG. 8.

The digital video processor of FIG. 8, which has been used in the above calculation of T1 is utilized, with respect to the remainder of the NMR system as shown in FIG. 9 with the item 16 corresponding to the digital video processor of FIG. 8 with the frame memories 18 storing the values, after calculation, of T1, T2, $M_0$. As a further note, once the value of T1 is found by the above method it requires but two passes through the video processor to obtain the value of $M_0$ from the equation $S1 = M_0[1-\exp(-TR1/T1)]$ because S1 is a measured value, $TR_1$ is known and T1 has been calculated.

In a second embodiment of the present invention the system of FIG. 8 is utilized in the calculation of the spin-spin relaxation time T2.

The NMR signals, in order to determine T2, are measured for fixed repetition time TR and for several echo times $TE_i$, $i=1, 2, \ldots N$. The known methods of calculation involve the use of reression techniques using a curve of the form P # exp $(-TE/T2)$ wherein P is defined as the pseudo-density which is the extrapolation of the measured signals back to a TE of 0 where P and T2 are adjusted so that the curve most closely matches the measured signal. In an instance where two different echo times TE1 and TE2 are utilized the signal $S_1$ is equated to P # exp $(-TE1/T2)$ and the signal S2 is equated to P # exp $(-TE2/T2)$ with the value TE1 being less than TE2. Utilizing these two equations for the values of S1 and S2 which are acquired through the memory 14 from the measurement means 10 as shown in FIG. 9, the circuit 16 of FIG. 9, shown in detail in FIG. 8, as the video processor circuit, performs the following manipulations on the input data S1 and S2.

In frame number 1 the value of S1 is stored and is passed through the look up table 77 to form the lnS1 which is stored back in frame number 1. Frame number 2 contains the measured value for S2 which is also passed through the look up table 77 to form lnS2 which is stored back in frame number 2. Once these two "passes" have occurred then in a third "pass" through the video processor, a difference image lnS1−lnS2 is formed and stored in frame number 1. These values are stored in the frame number 1 because the values for S1 and S2 are no longer necessary once the log values and the differential values have been formed. Thus the result of the subtraction of lnS1−lnS2 is stored in frame number 1. In the next pass through the video processor the difference values stored in frame 1 is multiplied by the quantity 1/(TE2−TE1) and stored in frame number 1. This result is the image of 1/T2. This value can be seen from an analysis of the ratio of S1 divided by S2 which equals P exp (−TE1/T2)/P exp (−TE2/T2). Thus each step or pass through the digital video processor provides for a solution to the above equation in terms of 1/T2. In a final pass through the digital video processor the reciprocal of 1/T2 is formed by means of the LUT 77 in order to obtain a T2 image which is stored in one of the frame memories. It can be seen that the calculation of T2 involved 5 passes through the digital video processor which takes approximately 5 times 1/30 seconds for a total time of 1/6 seconds. This is a significant improvement over that attainable by performing the calculations through a programmable microcomputer, which was accomplished in the prior art.

It should also be noted that the digital frame memories and the digital video processor could be used to provide both the T1 as indicated previously as well as the T2 as indicated in the aforementioned steps. The result would be such that, for example, T1 would be stored in frame memory number 1 and T2 would be stored in frame memory number 2 as an output which can be shown as containing the values in frame memories 18 for further processing in accordance with pulse sequence selection controls 22, as shown in FIG. 9, for example, in conjunction with the automated nuclear magnetic resonance image synthesis 20 which outputs the results through the DAC 24 to the display 26 which is extensively discussed in copending application Ser. No. 727,674 filed on Apr. 26, 1985. This copending application relates to the apparatus and a method for producing images on the interior of the body and more particularly produces synthesized computer images based on a minimal number of NMR measurements. It is also recognized that as presented hereinabove, the digital video processor of FIG. 8 of the present invention is distinct from the digital video processor 70 of FIG. 7 of the copending application Ser. No. 727,674. In other words the digital video processor of FIG. 8 of the present invention is an improved means for calculating the intrinsic parameters labeled 16 in FIG. 9 of the present invention and in FIGS. 2 and 7 of the copending application Ser. No. 727,674. It is also recognized by those skilled in the art that both of these digital video processors could be incorporated into a single digital video processor which is controlled by a microcomputer to perform not only the steps of acquiring T1 and T2 but also of providing pulse control for producing synthesized computer images based upon the acquired T1 and T2 images.

In a further embodiment of the present invention the digital video processor of FIG. 8 in conjunction with the showings of FIG. 9 can be utilized to calculate the value of T2 from an arbitrary N number of measurements. Once again because of the utilization of the digital video processor the algorithms which will be derived below for a N arbitrary number of measurements, will be processed in real time with the memories being used for storing original images, obtained from the measurement devices of a normal NMR, and the memories will be used for intermediate results as well as the final T2 image derived therefrom.

The spin-spin relaxation time T2, when based on the arbitrary number N of measurement at several echo times $TE_i$, $i=1, 2, \ldots N$ requires the use of regression techiques to fit a curve of the form P exp $(-TE/T2)$ wherein P is defined as the pseudo-density which is an extrapolation of the measured signals back to a TE of 0 where P and T2 are adjusted so that the curve most closely matches the measured signals. Utilizing the format wherein S (TE) is equal to $P \exp(-TE/T2)$, a linearized form is obtained by taking the logarithm whereby $\ln S = (\ln P) - (TE/T2)$. When 1/T2 is equal to m the equation takes the form of $\ln S - \ln P + mTE = 0$. For a given data set $(TE_i, S_i)$ P and m can be determined by the least squares method wherein $$R = \sum_i [\ln S_i - \ln P + mTE_i]^2$$

is minimized. The minimization conditions are derived from the partial derivatives being set equal to 0. Thus $$\delta R/\delta(\ln P) = \sum_i [\ln S_i - \ln P + mTE_i](-1) = 0 \text{ and } \delta R/\delta m =$$

$$\sum_i [\ln S_i - \ln P + mTE_i](TE_i) = 0.$$

From this we obtain $$(\ln P) - m \sum_i TE_i = \sum_i \ln S_i \text{ and } (\ln P) \sum_i TE_i - m \sum_i TE_i^2 =$$

$$\sum_i (\ln S_i) TE_i.$$

Using the above two equations and solving using a determinant form we have the determined $$D = -N \sum_i TE_i^2 + (\sum_i TE_i)^2$$

with the determinant D being a constant because each of the items $TE_i$ has no spatial dependence i.e., not dependent on X and Y, and therefore is a constant value which is known and can be computated for multiplication by the digital video processor as will be explained below.

Thus utilizing the determinant as a constant we have the following equation for $$\ln P = (1/D)[-(\sum_i \ln S_i)(\sum_i TE_i)^2 + (\sum_i (\ln S_i)(TE_i))(\sum_i TE_i)].$$

This will be hereinafter referred to as equation 1. The second equation to be known as equation number 2 is for the value of $$m = (1/D)[-N(\sum_i (\ln S_i)Te_i) + (\sum_i TE_i)(\sum_i \ln S_i)].$$

It is to be noted that N= the number of different values of TE.

Once again, it must be emphasized that the value for $S_i$ has a spatial dependence i.e., $S_i(x, y)$ while the values for $TE_i$ do not have a spatial dependence and are therefore known and can be a value which is provided as a constant for multiplication by the microprocessor 80 because of previous tabulation.

The two linear combinations equations 1 and 2 are thus set up to be solved by a series of passes through the digital video processor of FIG. 8 as will be explained.

The first function, after taking the log of Si, which must be formed by various pass throughs of the digital video processor, is the summation of the signal $\ln S_i$. Assume, for the purposes of detailing an example and as shown in the FIGS. 5 and 6 we have TE with four values and therefore i=4. This would lead to a series of signals $S_1$–$S_4$ being available from the measured outputs. If four signals are available then four frames are utilized and loaded with, for example, the signal $\ln S_1$–$S_4$ which are summed in a series of pass throughs which adds $\ln S_1$ to $\ln S_2$ and then the sum is added to $\ln S_3$ which in is added to $\ln S_4$ to obtain a value which is equal to $$\sum_i \ln S_i$$

for i=4. This value of $$\sum_i \ln S_i$$

would be stored, for example, in frame number 5. Then a pass through is made in order to calculate the term which is the summation of $\ln S_i$ times $$TE_i(\sum_i (\ln S_i)TE_i)$$

which evolves by multiplying each of the values of $\ln S_i$ in frames 1, 2, 3 and 4 by the values of TE1, TE2, TE3, TE4, respectively. Because the values $TE_i$ are known and constant they are formed microprocessor. The result of this $$\sum_i (\ln S_i)(TE_i)$$

is stored in frame number 6. It is of course to be noted that these various multiplications and additions are performed by the arithmatic logic unit ALU 76 and the multiplier 74 under the control of the microprocessor 80. At this point it must also be noted that although there are 6 frames shown as Examples in the frame memory structure 60, this is merely by way of example and the derivation of the equations for T2 will involve, according to the example given above and continued below, more frames than 6. Again it is to be noted that the use of 6 frames in the FIG. 8 is merely exemplary and the number of frames to be utilized can be increased or decreased to meet the needs of a particular calculation.

In order to form the first term for equatl mumber 1 the value stored 5 corresponding to $$\sum_i \ln S_i$$

multiplied by $$\sum_i TE_i^2$$

through the use of the multipliers 74 and stored in frame number 7. The second term of equation number 1 is performed by miltiplying the values stored in frame number 6 by $$\sum_i TE_i$$

and storing that value in frame number 8. Then the equation number 1 combines frame memories 7 and 8 through the arithmetic logic unit 76 and stores the sum frame number 9. Frame number 9 is then multplied by 1/D and stored in frame number 10 which now contains a value for the logarithm of P. A further pass through of the look up table provides the value for P which is stored in frame number 11, for example.

After the value for P has been determined the terms of the equation number 2 for the value of 1/T2 (m) are determined in the following order. The first term of equation number 2 involves the items stored in frame memory number 6 which is multiplied by $-N$ and stored in frame number 12. The second term of equation number 2 is formed by the combination of the contents of frame memory number 5 being multiplied by $$\sum_i TE_i$$

and storing the result in frame memory 13. Thus the pass through of the combination of frames 13 and 12 yields in frame 14 a value which corresponds to the two terms of equation number 2. This value is multiplied by 1/D in another pass through and the value of this multiplication is stored in frame number 15. Thus, frame number 15 contains a value equal to m or 1/T2. Another pass through for the inverse processing yields in frame 16 a value for T2.

It will be recognized that although 16 frames have been utilized in this calculation many of the extra frames are not necessary as some of the values can be replaced once they are no longer needed. For example, once the frame memory number 6 contains the value for $$\sum_i \ln S_i)(TE_i)$$

then there is no longer a need for the conten of frame memories 1–4.

It will also be recognized by those skilled in the art that other types of "passages" through the digital video processor could be accomplished to provide the results.

The result of the instrumentation and its usage with the NMR provides a system which can take initial NMR spin-echo measurements ($S_i(x, y)$ or $\ln S_i(x, y)$) and automatically determine the computed pseudo-density P and T2 images. The elapsed time is approximately equal to 2N+2 video frames which in the instance of a typical measurement of four values for N=10 frame passages of 1/30 seconds each for a total time of one-third of a second.

Obviously, numerous additional modifications and variations of the present invention, including the use of two or more repetition times and the subsequent change in algorithms necessary to change the T1 estimate at each echo-time or alternate ways to performing the T1 fit or the T2 fit, are possible in light of the above teachings. It must also be emphasized that although the spin-echo imaging technique has been utilized in the calculation of the examples for T1 and T2, other techniques including the use of an inversion recovery (IR) sequence, a partial saturation (PS) sequence or a modified spin-echo sequence may be utilized with the resultant equations necessary to determine the intrinsic values being solved through the use of digital video processor techniques. Another modification which could be easily implemented is the use of flip angles different from 90° with respect to the flipping of the longitudinal magnetization. It is therefore to be understood that within the scope of the appended claims, the invention may be practiced otherwise than as specifically described herein.

What is claimed as new and desired to be secured by Letters Patent of the United States is:

1. A method for determining the spin-lattice relaxation time T1 of an image during a Nuclear Magnetic Resonance (NMR) measurement technique on a human body comprising the steps of:

subjecting said body to magnetic fields in accordance with a NMR technique at two different predetermined stored pulse repetition times TR1 and TR2;

measuring a first signal S(TR1) at a first one (TR1) of said two repetition times including the steps of setting a longitudinal magnetization to zero, waiting a first period of time equal to a first pulse repetition time TR1, and then flipping the longitudinal magnetization MZ by 90° into the x-y plane wherein the value of x-y plane magnetization immediately after the step of flipping is said first signal, called the transverse magnetization, which is equal to the value of the longitudinal magnetization immediately prior to the step of flipping and wherein said first signal S(TR1) is expressed by a first equation $S(TR1) = M_0[1 - \exp(-TR1/T1)]$ where $M_0$ is a constant representing the net magnetization;

measuring a second signal at a second one (TR2) of said two repetition times including a step of setting a longitudinal magnetization to zero, waiting a second period of time equal to said second pulse repetition time TR2, and then flipping the longitudinal magnetization by 90° into the x-y plane, wherein the value of the x-y plane magnetization immediately after the step of flipping is said second signal, called the transverse magnetization, which is equal to the value of the longitudinal magnetization immediately prior to the step of flipping and wherein said measured second signal S(TR2) is expressed by a second equation $S(TR2) = M_0[1 - \exp(-TR2/T1)]$;

storing the value of said measured first signal in a first memory frame and the value of said measured second signal in a second memory frame;

inverting, through the use of a look-up table the value of said measured second signal stored in said second memory frame and storing said inverted value in said second frame memory;

multiplying the value of the contents of said first memory frame by the value of the contents of said second memory frame through the use of a microprocessor controlled multiplier in order to form a product R and storing said product R in said first memory frame;

mapping the value of R stored in said first memory frame to T1 in a microprocessor controlled look-up table using the transformation $R = [1 - \exp(-TR1/T1)]/[1 - \exp(-TR2/T1)]$;

the value T1 obtained from said transformation.

2. The method according to claim 1 wherein said step of inverting, said step of multiplying and said step of mapping in the look-up table, each constitute one passage through a digital video processor controlled by said microprocessor.

3. The method according to claim 2 wherein each passage through of said digital video processor requires approximately 1/30 seconds.

4. A method for determining the spin-spin relaxation time T2 of an image during a Nuclear Magnetic Resonance (NMR) measurement technique on a human body comprising the steps of:

subjecting said body to magnetic fields in accordance with a NMR technique at two different predetermined echo times TE1 and TE2 with TE1 being less than TE2;

obtaining a first measured value S1 corresponding to one of said two different echo times TE1;

obtaining a second measured value S2 measured at another one of said two different echo times TE2;

storing in a first memory frame said first measured signal S1 and storing in a second memory frame said second measured value S2;

mapping the value S1 in said first frame memory to lnS1 via a look-up table and storing the value of lnS1 in said first memory frame;

mapping the value of said second measured signal S2 in said first frame memory into lnS2 by means of said look-up table and storing in said second memroy frame the value of lnS2;

forming a difference image by means of said look-up table corresponding to lnS1-lnS2 and storing said value in said second memory frame;

multiplying in a microprocessor controlled multiplier the value stored in said second memory frame by the quantity 1/(TE2−TE1) and storing the result in said second memory frame; and taking the reciprocal of the value stored in said second memory frame by means of a look-up table and storing said reciprocal as the value of T2.

5. A method according to claim 4 wherein said steps of mapping the value S1, mapping the value S2, forming a difference image, multiplying and taking the reciprocal are each constituted by one passage through a digital video processor controlled by said microprocessor.

6. A method according to claim 5 wherein each passage through of said digital video processor requires approximately 1/30 seconds.

7. A method for determining the spin-spin relaxation time T2 of an image during Nuclear Magnetic Resonance (NMR) measurement technique on a human body comprising the steps:

subjecting said body to magnetic fields in accordance with a NMR technique at a plurality of predetermined echo times $TE_i$, $i=1, 2, \ldots N$;

obtaining a plurality of measured values $S(i)$ corresponding to each of said plurality of echo times $TE_i$;

obtaining the logarithm of each of said plurality of measured values by means of a look-up table;

storing said logarithms in a first plurality of memory frames;

summing the values in each of said plurality of frame memories by means of an arithmetic logic unit and storing in a first memory frame said summed value;

multiplying each of the values stored in said first plurality of memory frame by corresponding one of said plurality of echo times $TE_i$ by means of a microprocessor control multiplier and storing the value of the sum of said multiplications in a second memory frame;

multiplying the value stored in said first memory frame by the summation of the square of each of said plurality of echo times $TE_i$ and storing said muliplied value in a third memory frame;

multiplying the value stored in said second memory frame by the summation of each of the values of said echo times $TE_i$ and storing said multiplied value in a fourth memory frame;

adding together the value stored in said third and said fourth memory frames and storing the result in a fifth memory frame;

multiplying the value in said fifth memmory frame by a constant whose value is equal to $$1/(-N \sum_i TE_i^2 + (\sum_i TE_i)^2$$

and storing the results of multiplication in a sixth frame;

multiplying the value stored in said second memory frame by $-N$ and storing the result in a seventh memory frame;

multiplying the value stored in said first memory frame by the summation of $$TE_i(\sum_i TE_i)$$

and storing the result in a eighth memory frame;

adding together the values stored in said eighth memory frame and said seventh memory frame and storing said added result in a ninth memory frame;

multiplying said ninth memory frame by said constant and storing the result in a tenth memory frame; and inverting the value stored in said tenth memory frame and storing the result as the value for T2 in said eleventh memory frame.

8. A method according to claim 7 wherein each of said steps of adding, multiplying and inverting are accomplished by passages through a digital video processor controlled by said microprocessor.

9. The method according to claim 7 wherein each passage through of said digital video processor requires approximately 1/30 seconds.

* * * * *